(12) United States Patent
Ng

(10) Patent No.: US 11,992,726 B2
(45) Date of Patent: May 28, 2024

(54) ADJUSTABLE PERINEOMETER DEVICE

(71) Applicant: Bioinfinity (M) Sdn. Bhd., Kuala Lumpur (MY)

(72) Inventor: Shea Kang Ng, Kuala Lumpur (MY)

(73) Assignee: Bioinfinity (M) Sdn. Bhd., Kuala Lumpur (MY)

( * ) Notice: Subject to any disclaimer, the term of this patent is extended or adjusted under 35 U.S.C. 154(b) by 214 days.

(21) Appl. No.: 17/458,527

(22) Filed: Aug. 26, 2021

(65) Prior Publication Data

US 2022/0062700 A1    Mar. 3, 2022

(30) Foreign Application Priority Data

Sep. 1, 2020    (MY) .............................. PI2020004513

(51) Int. Cl.
  *A63B 23/20*    (2006.01)
  *A63B 21/00*    (2006.01)
  *A63B 21/02*    (2006.01)

(52) U.S. Cl.
  CPC ........ *A63B 23/20* (2013.01); *A63B 21/00061* (2013.01); *A63B 21/028* (2013.01); *A63B 2220/51* (2013.01); *A63B 2220/80* (2013.01)

(58) Field of Classification Search
  CPC ................................ A63B 23/20; A61B 5/227
  See application file for complete search history.

(56) References Cited

U.S. PATENT DOCUMENTS

| | | | | |
|---|---|---|---|---|
| 5,674,238 A | * | 10/1997 | Sample | A61B 5/4337 606/192 |
| 5,787,892 A | * | 8/1998 | Dabney | A63B 23/20 600/593 |
| 6,468,232 B1 | * | 10/2002 | Ashton-Miller | A61B 5/227 600/593 |
| 2004/0030360 A1 | | 2/2004 | Eini et al. | |
| 2006/0036188 A1 | | 2/2006 | Hoffman et al. | |
| 2008/0139876 A1 | * | 6/2008 | Kim | A63B 24/00 600/29 |
| 2011/0263396 A1 | | 10/2011 | Hung | |
| 2013/0144191 A1 | * | 6/2013 | Egorov | A61B 5/227 600/591 |

(Continued)

FOREIGN PATENT DOCUMENTS

| | | | |
|---|---|---|---|
| WO | WO-2014176689 A1 | * 11/2014 | ............. A61B 5/227 |
| WO | 2016/042310 A1 | 3/2016 | |

OTHER PUBLICATIONS

Bioinfinity (M) Sdn Bhd; EP Application No. 21192947.6; EP Search Report; The Hague, dated Jan. 18, 2022, 10 pp.

*Primary Examiner* — Nyca T Nguyen
(74) *Attorney, Agent, or Firm* — FisherBroyles LLP; Anthony J DoVale

(57) ABSTRACT

Embodiments relate to perineometer device for providing accurate biofeedback. In an embodiment, the device comprises a cap, at least one first finger and at least one plate, at least one battery for applying an electrical potential difference to the at least one first finger and the at least one plate, a capacitive measuring microchip for measuring capacitance between the at least one finger and the at least one plate and a processor for recording capacitance measured by the capacitive measuring microchip and transmitting capacitance value or force data to a user interface device via radio frequency.

16 Claims, 16 Drawing Sheets

(56) References Cited

U.S. PATENT DOCUMENTS

| | | | | |
|---|---|---|---|---|
| 2014/0088471 | A1* | 3/2014 | Leivseth | A61B 5/227 |
| | | | | 601/89 |
| 2016/0279468 | A1* | 9/2016 | Hung | A63B 23/20 |
| 2016/0346610 | A1* | 12/2016 | Iglesias | A61B 5/227 |
| 2020/0093413 | A1* | 3/2020 | Hennings | A63B 21/0023 |

* cited by examiner

ADJUSTABLE PERINEOMETER DEVICE

FIELD OF THE INVENTION

The present invention relates to a perineometer device for sphincter muscle exercise.

BACKGROUND OF THE INVENTION

Weakened pelvic floor muscles lead to internal organs not being fully supported by the muscles and cause difficulty controlling the release of urine, feces or flatus. Pelvic floor exercises are designed to strengthen the pelvic floor muscles and to prevent the need for corrective surgery. Strengthening the training of the pubic muscle can promote the function of the urethra and anal sphincters, preventing urinary incontinence and anal incontinence.

U.S. Pat. No. 8,088,051 B2 discloses an adjustable sphincter exerciser (Kegel exercise) that includes a flexible tubular member, at least one sleeve mounted to the tubular member; a body inserted into the tubular member, a conductive device connected to body and located in the tubular member, the conductive device being activated when the tubular member is compressed, a vibration unit electrically connected to the conductive device, and a power unit providing power to the conductive device and the vibration unit. The at least one sleeve can be replaced and has different hardness, when the user squeezes the at least one sleeve and the tubular member to activate the conductive device and the vibration unit, the user is acknowledged the force that sphincter is exercised. In this arrangement, when the tubular member is squeezed by the sphincter, bent portions of conductive plate contact metal portion to form a conductive loop to generate biofeedback signals. This patent does not disclose a component to sense and measure force when the tubular member is compressed.

U.S. Pat. No. 7,628,744 B2 discloses a multi-mode pelvic exercise probe comprising a pressure sensing circuitry and components that provide audio/visual biofeedback signals. Conventional sphincter exerciser may comprise a means to sense and measure pressure when the tubular member is compressed. However, most pressure or force sensors are not able to detect sphincter muscle contraction with high accuracy, repeatability and sensitivity, hence producing inaccurate readings.

In view of the shortcoming, it is desirous to provide a perineometer device with a high accuracy sensor to detect force of muscular contractions.

SUMMARY OF THE INVENTION

The present invention relates to a perineometer device for providing accurate biofeedback signals on the condition of sphincter muscle, comprising a cap coupled to a tubular member, at least one finger, at least one beam plate or at least one force sensing resistor disposed coaxially within the tubular member such that the at least one plate or force sensing resistor is within the at least one finger, means for applying an electrical potential difference to the at least one finger and the at least one plate, a sensor to measure capacitance therefrom or the at least one force sensing resistor receiving force applied to the at least one finger and a processor connected to the sensor measuring capacitance or to the at least one force sensing resistor.

BRIEF DESCRIPTION OF THE ACCOMPANYING DRAWINGS

The present invention will be fully understood from the detailed description given herein below and the accompanying drawings which are given by way of illustration only, and thus are not limitative of the present invention, wherein:

In the appended drawings:

FIG. 1a shows a perspective front view of the adjustable perineometer device in accordance to the present invention FIG. 1b shows a perspective back view of the adjustable perineometer device in accordance to the present invention FIG. 2a shows an exploded view of a first embodiment of the device wherein parallel beam plate mechanism is featured FIG. 2b shows a perspective view of the device wherein a conductive mesh is featured instead of at least one finger FIG. 3a shows a cross-sectional view of the present invention according to the first embodiment FIG. 3b shows a capacitive sensing electronic configuration according to the first embodiment FIG. 4 shows a cross-sectional view of the present invention with the embodiment described in FIG. 3a when the at least one finger is fully extended FIG. 5 shows an exploded view of a second embodiment of the present invention wherein force sensing resistor is used instead of parallel beam plate mechanism FIG. 6a shows a cross-sectional view of the present invention according to the second embodiment FIG. 6b shows a force sensing electronic configuration according to the second embodiment FIG. 7 shows a cross-sectional view of the present invention with the embodiment described in FIG. 6a when the fingers are fully retracted and force sensing resistor is used instead of parallel plates FIG. 8 shows a cross-sectional front view of the cap in either one of the embodiments FIG. 9 show a force map for a user with healthy sphincter muscle FIG. 10 show a force map for a user with a localized tear in the sphincter muscle FIG. 11 show a force map for a user with a more extensive muscular or neurological damage FIG. 12 show a force map for a user after implementing exercise routine with the adjustable perineometer device FIG. 13 shows a force map for a user with involuntary contractions (vaginismus)

FIG. 14 show a force graph for users following exercise routine with the adjustable perineometer device after two months FIG. 15 show a force graph for a user suffering from vaginismus after two months

DETAILED DESCRIPTION OF THE INVENTION

Detailed description of preferred embodiments of the present invention is disclosed herein. It should be understood, however, that the embodiments are merely exemplary of the present invention, which may be embodied in various forms. Therefore, the details disclosed herein are not to be interpreted as limiting, but merely as the basis for the claims and for teaching one skilled in the art of the invention. The numerical data or ranges used in the specification are not to be construed as limiting. The following detailed description of the preferred embodiments will now be described in accordance with the attached drawings.

A sphincter is a specialized circularly shaped muscle that should contract uniformly and the resulting force from that contraction should be radially consistent. Damage to the muscle in the form of a tear or other physical trauma, or neurological damage could result in inconsistent contraction of the muscle and therefore inconsistent force applied radially when the muscle is contracted. Knowledge of the underlying physiology with women suffering incontinence or related condition would be aided by gathering force data during training and exercise periods. This data provides a user or medical personnel a feedback on the condition of the sphincter muscle.

The present invention relates to an adjustable perineometer device for providing accurate biofeedback on the condition of sphincter muscle, specifically female pubococcygeal and related perineal sphincter musculature. The biofeedback helps users to identify, develop, train and condition and rehabilitate the sphincter muscle.

The adjustable perineometer device features a self-contained perineometer probe for intravaginal use, communicating to a user device through a wireless means such as radio frequency (RF) using a RF transmitter and RF receiver wherein the user device includes a software or application to process and display the biofeedback based on data received from the device. The software or application provides the user an analytical format of data for the user's review. Further, it provides the ability to customize exercise routines. The adjustable perineometer device shall be explained in mainly two embodiments—first embodiment featuring a parallel beam plate as a sensing mechanism and second embodiment featuring a force sensing resistor as a sensing mechanism.

FIGS. 1-8 show the present invention in multiple embodiments from various views. The present invention comprises a cap (1), a setting indicator (2), a power switch (3), a status light (4), a detent (5), a planetary gear set (6), an adjusting screw (7), a first anchor (8a), a second anchor (10a), a tubular member (11), an acme thread (12), a circuit board (13), a case (14), at least one battery (15), a biasing means (16), at least one first finger (9a) and parallel plate (18) for the first embodiment and a third anchor (8b), a fourth anchor (10b), at least one second finger (9b) and force sensing resistor (17) for the second embodiment.

FIGS. 1a and 1b shows a front and back perspective view of the adjustable perineometer device respectively in accordance to the present invention. The device comprises a cap (1) coupled to a tubular member (11) that houses electronics such as sensor mechanism and vibration device located internally. The tubular member (11) includes a flange-like protrusion (11a) at one end, a tube (11b) and a hemispherical end (11c) at the other end wherein upon inserting the adjustable perineometer device into an intravaginal cavity, the flange-like protrusion (11a) rest on the outer entrance to the intravaginal cavity while the hemispherical end (11c) is introduced further into the intravaginal cavity. The tubular member (11) is a malleable sheath that can transmit force to internal components. The tubular member (11) is made from medical grade silicone rubber, having range of force detectable of 0.1 N to 10 N. Alternatively, any soft and medical grade material may be used. In a non-limiting example, the sheath may be a material with high sensitivity to force so that the sensitivity of readings can be increased. The tubular member (11) is watertight to prevent any liquid from entering the tubular member (11). The cap (1) houses basic functional features such as but not limited to a setting indicator (2), a power switch (3) and a status light (4). The power switch (3) functions to power on/off the present invention. The status light (4) functions to indicate whether the present invention is on/off and possibly other indications such as but not limited to in training and pause. The status light (4) is a multiple color LED light that indicates different color light for different statuses. The setting indicator (2) functions to indicate type of settings the device is on, for example the force ranges detected by the invention. It is contemplated that a touch screen interface may replace the functional features wherein the settings of the device are controlled through touch-screen interactions. Optionally, the cap (1) includes a port for a wired connection to connect to a user device such that if the functional features on the cap (1) and/or wireless means of the invention is faulty, data is receivable and transmittable to user device through the wired connection to control the adjustable sphincter settings, process data and display to the user.

FIG. 2a shows an exploded view of the first embodiment of the device wherein parallel beam plate mechanism is featured. The cap (1) houses a circuit board (13) nestable within a circuit board frame (13a). The circuit board (13) comprises a processor to process signals, an RF transmitter (not shown) and receiver (not shown) for transmitting and receiving data. At least one battery (15) is to power the electronics in the device and for applying an electrical potential difference to the at least one first finger (9a) and at least one plate (18) so that capacitance can be measured. The planetary gear set (6) is rotatable corresponding to rotation of the cap (1) and functions to turn an adjusting screw (7) wherein the first anchor (8a) rides the adjusting screw (7). A detent (5) functions to adjust the position of the first anchor (8a). Turning the cap (1) in one direction rotatably urges the first anchor (8a) towards the cap (1) and turning the cap (1) in the opposite direction rotatably urges the first anchor (8a) away from the cap (2). At least one first finger (9a) is fixed coaxially to a case (14) at one end and fixed to the second anchor (10a) at the opposite end. The first anchor (8a) is nestable in the case (14) when in assembly. The at least one first finger (9a) is within the tubular member (11) and preferably, the at least one first finger (9a) is contactable or securable to the inner surface of the tubular member (11). The at least one first finger (9a) may be a rigid or malleable structure, preferably made up of segments like a chain wherein it is held in place at its ends. Turning the cap (1) in one direction retracts or extends the at least one first finger (9a) thereby decreasing or increasing relative stiffness of the at least one first finger (9a) resulting in increasing or decreasing the force necessary to deflect the at least one first finger (9a) by the muscle contraction. The at least one first finger (9a) is covered in a malleable sheath that transmits force generated during a muscle contraction to the finger assembly. In an alternative embodiment, a conductive means such as but not limited to a conductive mesh (20) is used instead of the at least one first finger (9a) as shown in FIG. 2b wherein in assembly the conductive mesh (20) encapsulates at least one plate (not shown) positioned internally to the conductive mesh (20).

FIG. 3a shows a cross-sectional view of the present invention according to the first embodiment. In assembly, at least one plate (18) is positioned internally, coaxially and parallel to the at least one first finger (9a) such that the at least one first finger (9a) and the at least one plate (18) are spaced apart when no force is applied to the at least one first finger (9a). Alternatively, a conductive means such as but not limited to a grid of conductive plates can be used instead of at least one plate (18). Preferably, at least one conducting protrusion is disposed perpendicular to the at least one first finger (9a) and at least one plate (18) with a small gap in between the protrusions wherein the protrusions facilitates a more accurate capacitance measurement. The battery (15) applies electrical potential difference to the at least one first finger (9a) and at least one plate (18) so that capacitance can be measured. An Analog Systems AD7746 microchip is used to measure the capacitance between the at least one first finger (9a) and at least one plate (18). FIG. 3b shows a capacitive sensing electronic configuration according to the first embodiment. The microchip (19) in combination with the at least one first finger (9a) and at least one plate (18) functions as capacitive sensors. In a non-limiting example, other type of capacitive measuring microchip known in the industry can be used. Referring back to FIG. 3a, the capacitive sensors form individual segments that are connected end to end. Preferably, each end of the individual segments is supported by one or more biasing means (not shown) wherein the biasing means (not shown) is a spring or spring-like material. The biasing means (not shown) in its nature provide a physical resistance. The biasing means (not shown) is attached to each end of the at least one plate (18) via a slidable guide so that the biasing means (not shown) is slidable up and down to apply varying amounts of physical resistance to the at least one plate (18) from 0 N to a desired amount of force by way of an extension and retraction mechanism. A plurality of biasing means (not shown) can be used to provide more control through increase in physical resistance. The strain measurements of the spring can be combined with the capacitance measurement to calculate the force, and also deduce the position of the applied force on the electrode. Alternatively, the at least one first finger (9a) and at least one plate (18) may have a soft material between them such as but not limited to a foam, rubber, soft plastic and other soft material known in the art. The soft material aids the at least one first finger (9a) to return back to its original position. The at least one first finger (9a) is such that the force generated by the muscle contraction causes deflection on the at least one first finger (9a). Deflecting the at least one first finger (9a) reduces gap in between the at least one first finger (9a) and the at least one plate (18) and therefore changing capacitance wherein larger deflection results in higher the capacitance change. The capacitance is calibrated wherein capacitance between the at least one first finger (9a) and the at least one plate (18) is recorded prior to no force being applied on the at least one first finger (9a) as a reference point for measuring the difference to when a force is applied to the at least one first finger (9a). The capacitance is measured by a capacitance sensor will be recorded by the processor.

FIG. 4 shows a cross-sectional view of the present invention with the embodiment described in FIG. 3a when the at least one first finger (9a) is fully extended. The at least one first finger (9a) is fixed on the second anchor (10a), passing through the fourth anchor (10b) and fixed on the case (not shown) that is connected to the circuit board (13). The circuit board (13) nesting onto a circuit board frame is extended out of the cap (1) and the at least one first finger (9a) stiffens.

FIG. 5 shows an exploded view of the second embodiment of the present invention. Force sensing resistor (shown in FIG. 6a) is used instead of parallel beam plate mechanism. Unlike the first embodiment which uses a planetary gear set, the cap (1) includes an acme thread (12) on which the circuit board frame (13a) rides. The circuit board (13) is nestable within the circuit board frame (13a). Turning the cap (1) in one direction urges the circuit board (13) towards the cap (1) and turning in the opposite direction urges it away from the cap (1) through the adjusting screw (7) and first anchor (8a). It is noted that the movement mechanism may be interchangeable for either embodiments and is not described here for parallel beam plate mechanism or force sensing resistor mechanism. At least one battery (15) is to power the electronics in the device. At least one second finger (9b) is fixed coaxially to the circuit board (13) at one end and fixed to the fourth anchor (10b) at the other end. In assembly, the at least one second finger (9b) passes through fourth anchor (10b) that functions to hold the at least one second finger (9b) in position. Withdrawing the circuit board (13) towards the cap (1) retracts the at least one second finger (9b), decreasing relative stiffness and resulting in decrease of force necessary to deflect the at least one second finger (9b). Similar to the first embodiment, the at least one second finger (9b) is within the tubular member (11) and preferably, the at least one second finger (9b) is contactable or securable to the inner surface of the tubular member (11) for transmitting force from muscle contraction to the finger assembly. Force range can be calibrated depending on the position of the first anchor (8a) such that a longer finger shifts sensing sensitivity to a low range, a shorter finger shifts the sensing sensitivity to a high range.

FIG. 6a shows a cross-sectional view of the present invention according to the second embodiment. In assembly, the at least one force sensing resistor (17) is grounded on a component and connected to a circuit board (not shown). The at least one force sensing resistor (17) is internally contactable and coaxially with the at least one second finger (9b) such that force applied to the at least one second finger (9b) will be transmitted to the at least one force sensing resistor (17) and measured as resistance by the at least one force sensing resistor (17). FIG. 6b shows a force sensing electronic configuration according to the second embodiment. The resistance is recorded by processor on the circuit board (not shown). The force sensing resistor (17) used is Tekscan Flexiforce A201.

Alternatively, the force sensing resistor (17) can be replaced by an accelerometer sensor such as NXP MMA8451 or an eddy current sensor such as Micro-Epsilon eddyNCDT 3005. Referring back to FIG. 6a, the biasing means (not shown) is attached in between the at least one second finger (9b) and force sensing resistor (17) via a slidable guide so that the biasing means (not shown) is slidable up and down to apply varying amounts of physical resistance to the at least one plate (18) from 0 N to a desired amount of force by way of an extension and retraction mechanism. Alternatively, the at least one second finger (9b) and the force sensing resistor (17) have a soft material between them such as but not limited to a foam, rubber, soft plastic and other soft material known in the art. The soft material aids the at least one second finger (9b) to return back to its original position. The resistance is calibrated wherein force sensing resistor (17) measures the resistance prior to no force being applied on the at least one second finger (9b) as a reference point for measuring the difference resistance to when a force is applied to the at least one second finger (9b).

FIG. 7 shows a cross-sectional view of the present invention with the embodiment described in FIG. 6a when the fingers are fully retracted and force sensing resistor (17) is used instead of parallel plates (18). The fingers are retracted between the third anchor (8b) and the fourth anchor (10b).

FIG. 8 shows a cross-sectional front view of the cap (1) in either one of the embodiments. The cap (1) has three possible stiffness settings, position 1-3, providing three possible force ranges. It is conceived that more than three rotatable positions may be provided wherein each position provides a different force range or a different stiffness of fingers. When using phosphor bronze fingers and 0.35 mm thick by 10 mm wide by 50 mm maximum effective length, the force range for position 1 is between 0.3-2.5 N, position 2 is between 0.5-5.0 N and position 3 is between 1.2-12 N.

It is contemplated that decreasing and increasing the relative stiffness of the at least one first finger (9a) can be achieved by other means such as but not limited to a push and pull lock mechanism wherein the at least one first finger (9a) is connected to a connection means through the cap (2). Retracting and extending of the at least one first finger (9a) is manipulated through moving the at least one first finger (9a) towards the cap (1) or away from the cap (1) respectively. The position of the connection means may be locked through rotating the at least one first finger (9a) when a desired length is achieved wherein by rotating the at least one first finger (9a), a ridge disposed on the connection means sinks into a corresponding ridge from a corresponding component. The corresponding component may have multiple corresponding ridges wherein the ridge on the connection means is lockable onto a specific corresponding ridge of the corresponding component, depending on the length of the at least one first finger (9a) to be achieved. It is also contemplated that decreasing and increasing the relative stiffness of the at least one first finger (9a) can be achieved by replacing fingers with different stiffness.

Preferably in both embodiments, four fingers are coaxially disposed in the device with four plates/force sensing resistors disposed internally to the at least one finger wherein a plurality of sensors, being either a capacitive sensor or a resistance sensor to measure capacitance or resistance of the at least one deflected finger upon force. The position of each sensor senses force from a specific radial area of the intravaginal cavity. It is contemplated that more number of fingers can be used to detect contraction from multiple intravaginal radial areas and not limited to only the x-axis and y-axis.

In the first embodiment, the deflection is sensed by energizing the finger (9a) and parallel plate (18) with electrical potential difference from the battery (15) and capacitance is measured by the sensor. Deflection of the finger (9a) changes the spacing of the finger (9a) and parallel plate (18) and therefore changes the capacitance. Characterizing the deflection versus capacitance curve can accurately determine finger to plate spacing and therefore applied force.

In the second embodiment, the finger (9b) are calibrated to yield accurate and repeatable force measurements by using of a force sensing resistor (17) positioned under the finger (9b) wherein when force is applied to the finger (9b), the finger (9b) deflects wherein the resistance is in relation to the amount of deflection. The simply supported finger deflects a known amount based on the formula:

$$\text{delta} = PL^3/48EI$$

where: delta is the deflection of the finger
P is the concentrated applied load to center of the finger
L is the length of the finger between supports
E is the Young's modulus of the material of the finger and
I is the moment of inertia of the finger Since the deflection is proportional to the length of the finger cubed, retracting the finger by a small amount significantly changes the force range. The invention envisions retracting the fingers into the cap effectively retracting the finger and changing the force range of the sensor substantially.

It is conceived that the deflection of the finger from both embodiments can be detected by sensors such as but not limited to ultrasonic, infrared distance, laser, inductance sensors and other deflection measuring sensors known in the art.

The invention described is operable in pre-programmed routines developed into a software/application and provide users with an option to customize their own exercise routines suited to their training protocol. In a non-limiting example, the pre-programmed routines may be an exercise routine to prompt contraction and relaxation periods together with selectable resistance to strengthen the sphincter muscle and sense the state of contraction of the sphincter muscle and prompt relaxation, including lowering resistance enabling sensing of fully relaxed muscles for women suffering from vaginismus. Prior to the training, users may select a suitable force range that may suit their condition by turning the cap to a specific position.

The capacitive sensors and the force sensing resistor are sensitive up to 0.1 N and provides good repeatability and accuracy. The RF transmitter transmits data such as force calculation received from the processor to a user device. The user device comprises a display unit and runs a software/application that processes the force data and translates it into a force map which is stored in the user device for the user's review. In a non-limiting example, force data stored in the user device includes routine used and time stamped data from each sensor during the training routine. The force map generated by the data collected displays areas of weaknesses of the muscle such as but not limited to tears and damaged tissue. The force maps aid in devising training routines as well as map results over time to document adherence to the prescribed regimen and encourage use by showing progress over time. The force maps may also aid medical practitioners to devise a specific treatment for the user. With the sensitive sensors providing good repeatability and accuracy on data measured, the present invention is able to provide accurate biofeedback.

The present invention comprises an internal vibrator device such as but not limited to a motor-driven vibrator or a piezoelectric vibrator, that provides tactile feedback to reinforce learned control to the user. The tactile feedback may provide vibrating signals such as but not limited to alerts for notifying the user on training routine timeline and stages, such as but not limited to beginning of the program, end of the program, continuing to a next training routine stage.

In a working example, four 0.35 mm thick, by 10 mm wide by 50 mm maximum effective length phosphor bronze fingers are coaxially disposed in the tubular member (11) with four phosphor bronze plates disposed internally each corresponding to each finger. Electrical potential difference is applied from the battery (15) to the at least one first finger (9a) and the at least one plate (18). Four capacitive sensors are disposed in the tubular member (11) to measure the initial capacitance and capacitance of the at least one deflected finger upon force. The device is switched on through the power switch (3) wherein the status light (4) will indicate that the device is switched on. The cap (1) is rotatable to any of the positions to achieve a specific force range, for example position 1 between 0.3-2.5 N, position 2 between 0.5-5.0 N and position 3 between 1.2-12 N. The cap (1) is turned on position 1 wherein the setting indicator (2) indicates the device being in position 1. A user device is paired to the device via radio frequency, specifically, Bluetooth. Once connected, the device transmits force data to the user device and the data is stored in the user device. The force data are shown in force maps and force graphs on the user device.

FIG. 9 shows a force map for a user with healthy sphincter muscle. In this figure it is seen that the forces are approximately equal throughout the circumference of the device (all four sensor outputs approximately equal) indicating that there is unlikely to be any neural or muscular damage to the user's sphincter muscle.

Figure 1A:
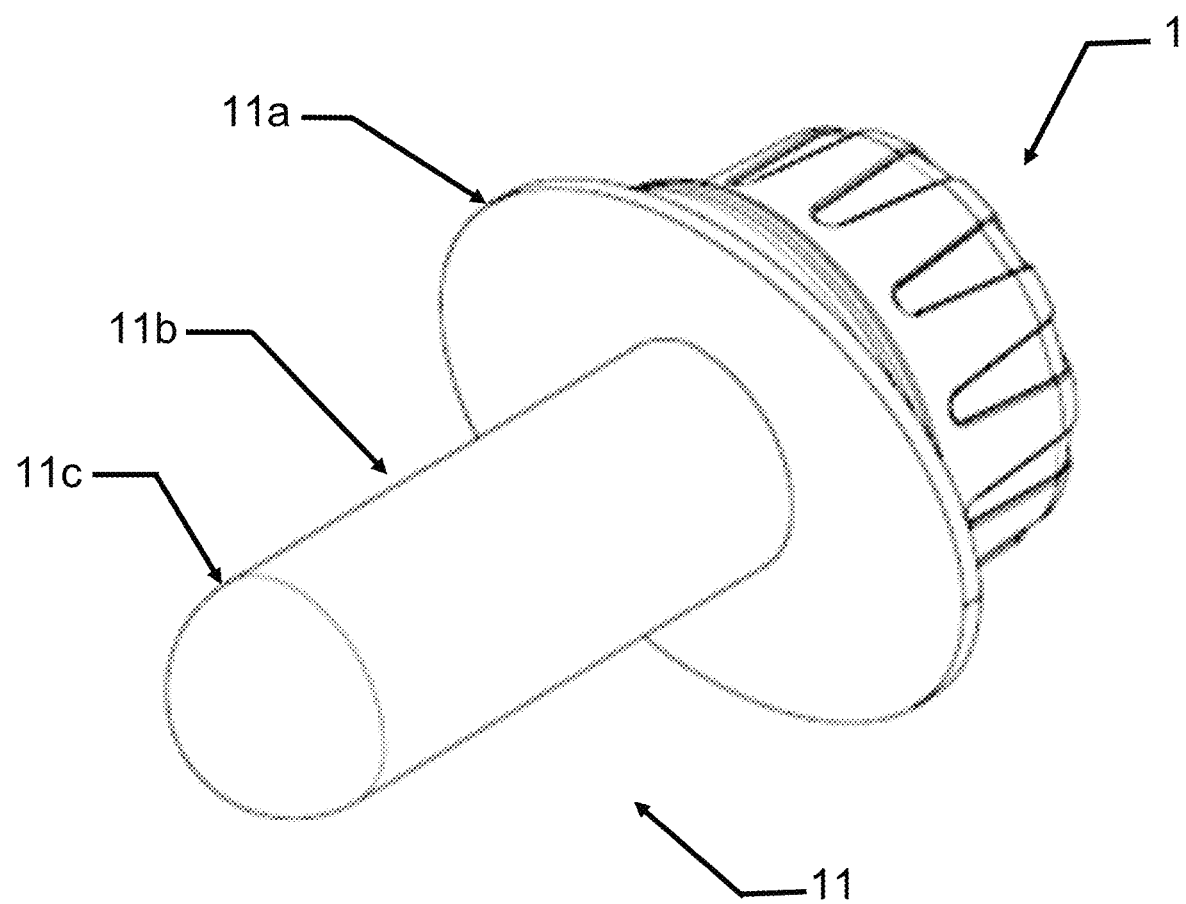
Figure 1B:
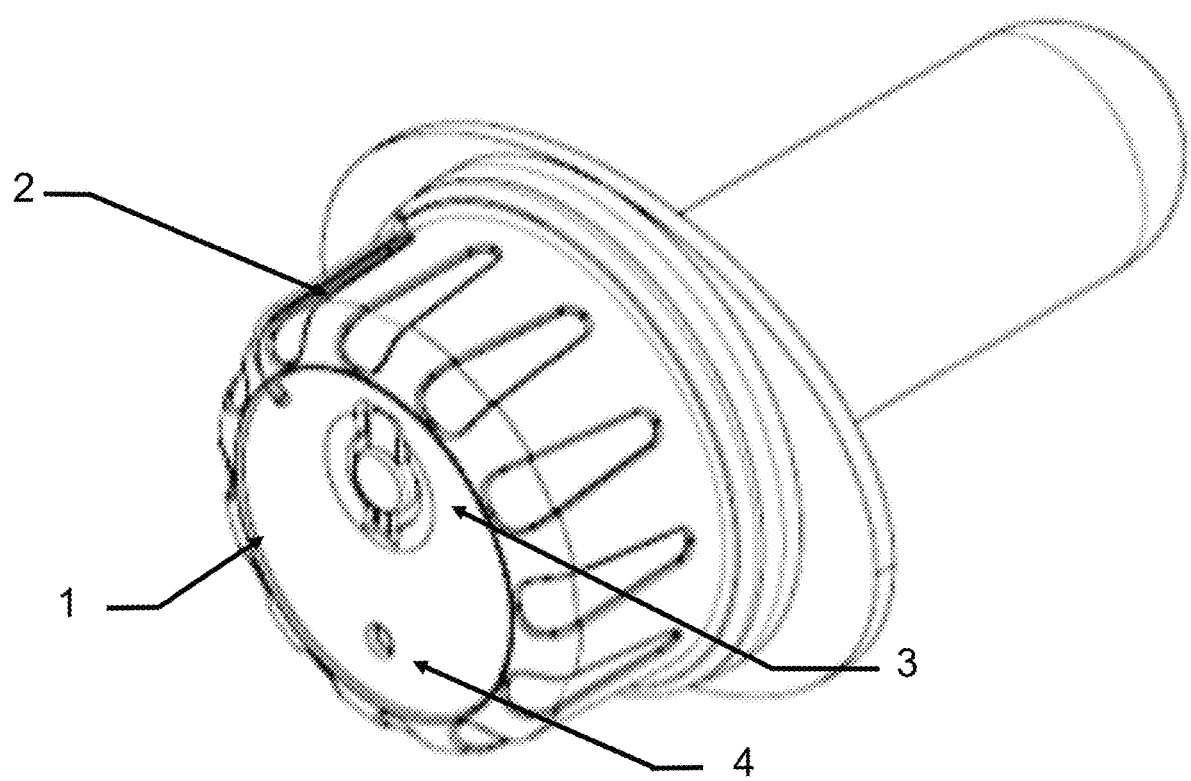
Figure 2A:
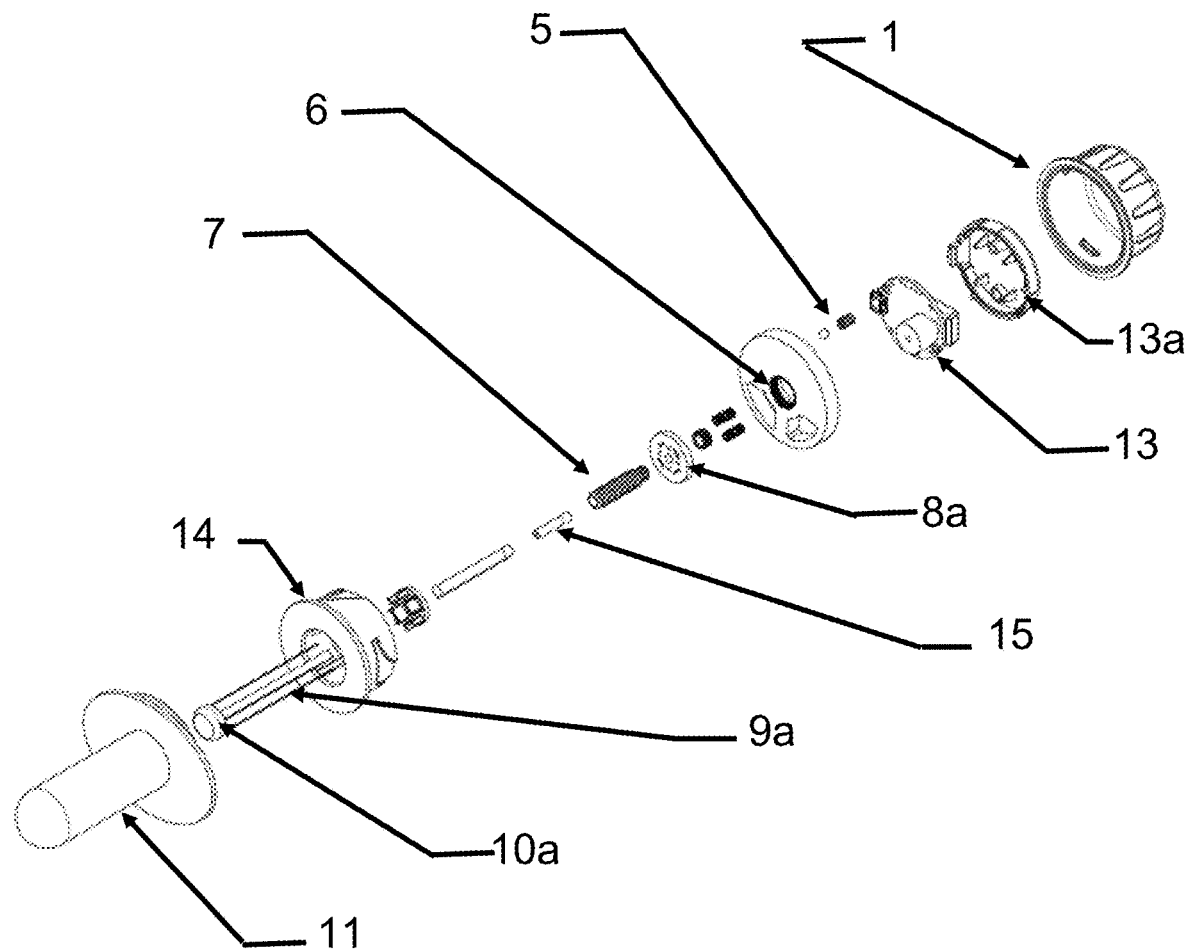
Figure 2B:
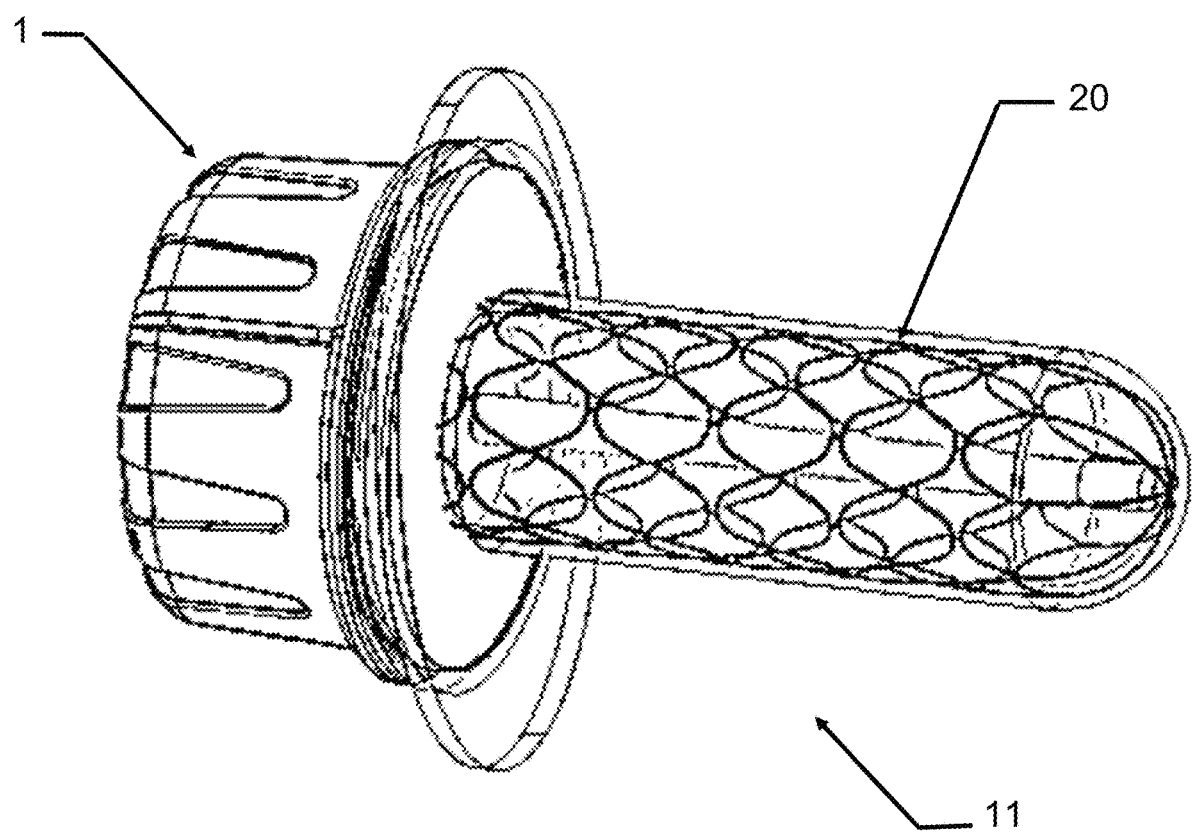
Figure 3A:
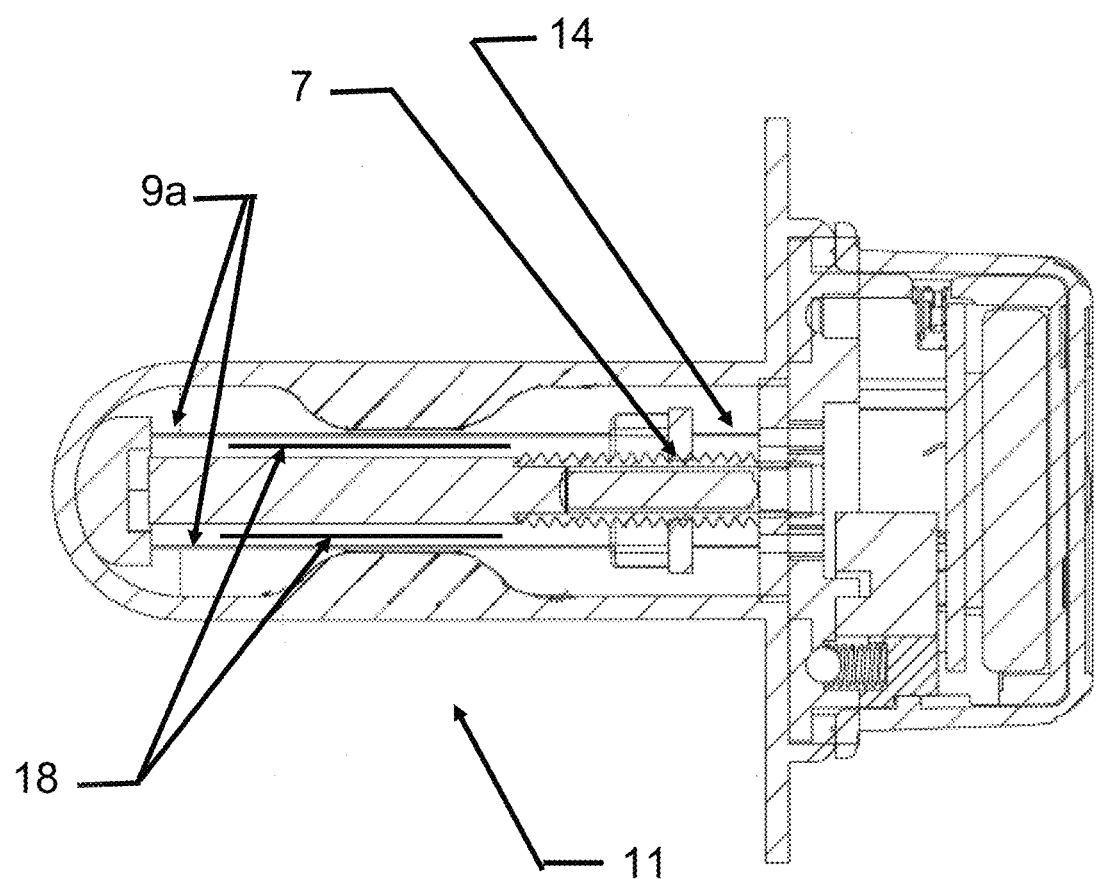
Figure 3B:
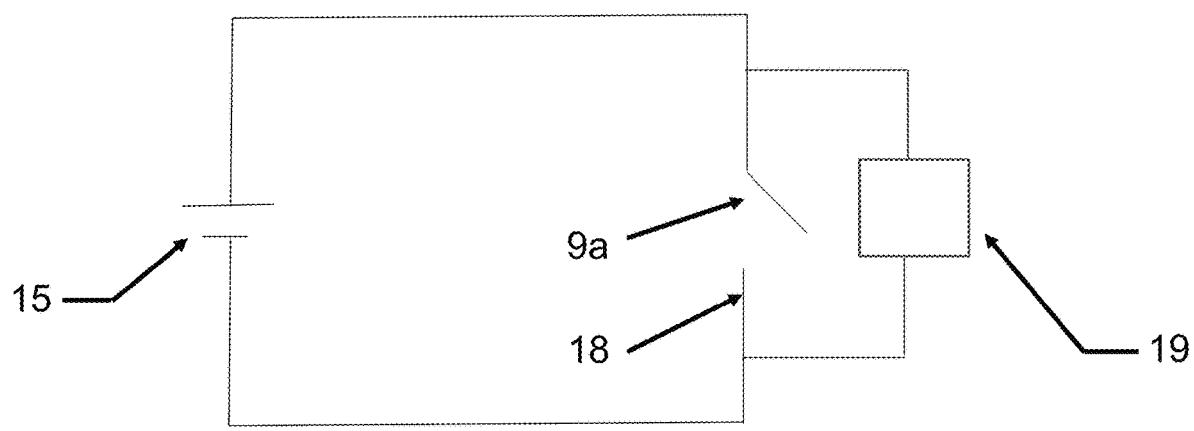
Figure 4:
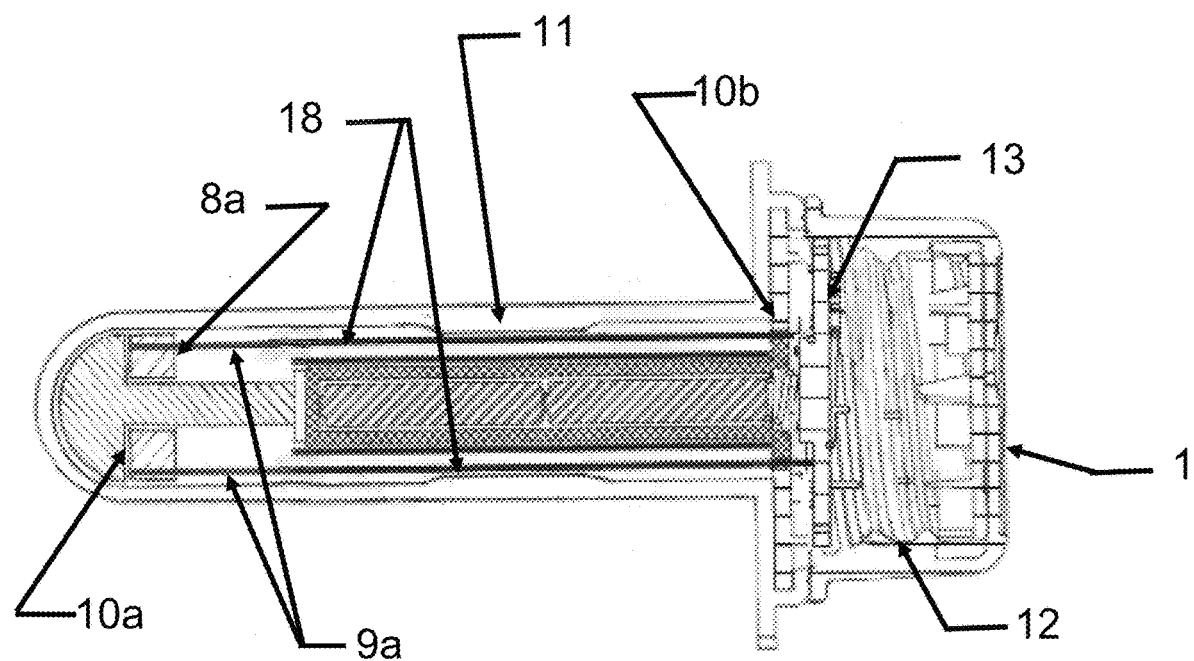
Figure 5:
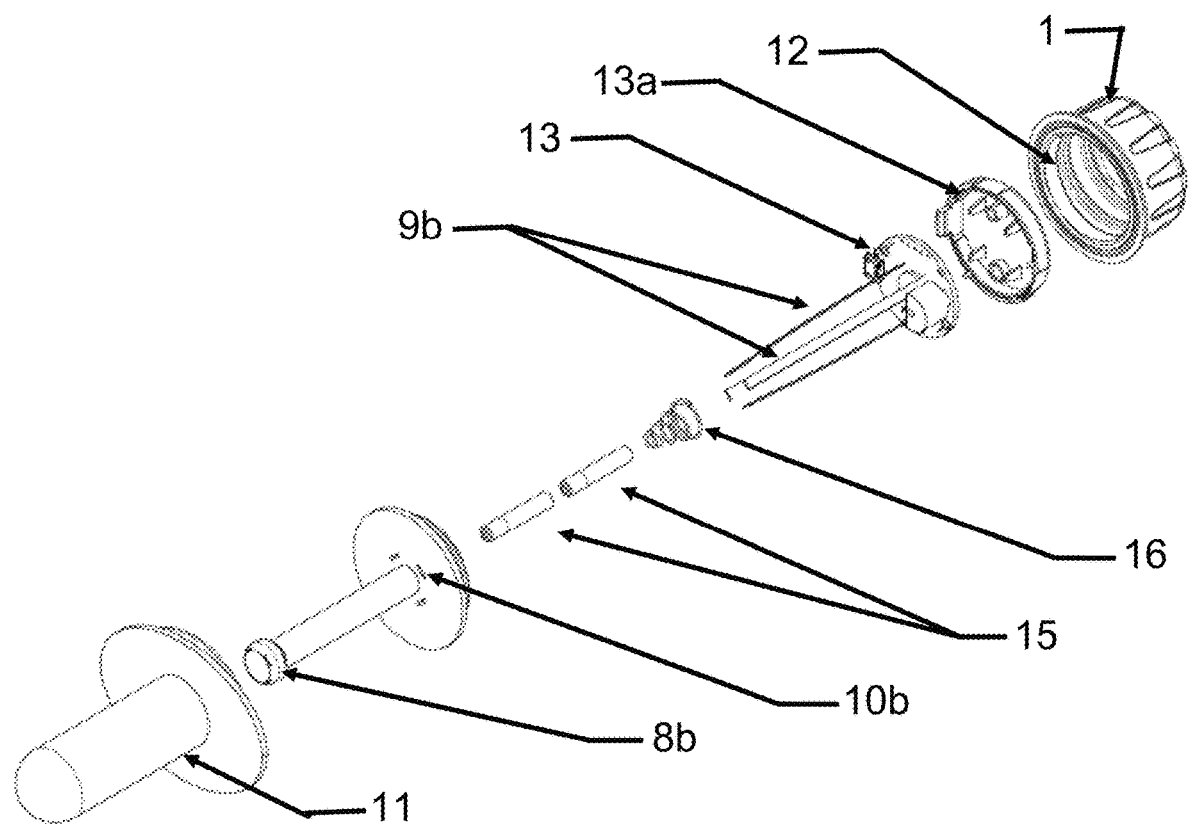
Figure 6A:
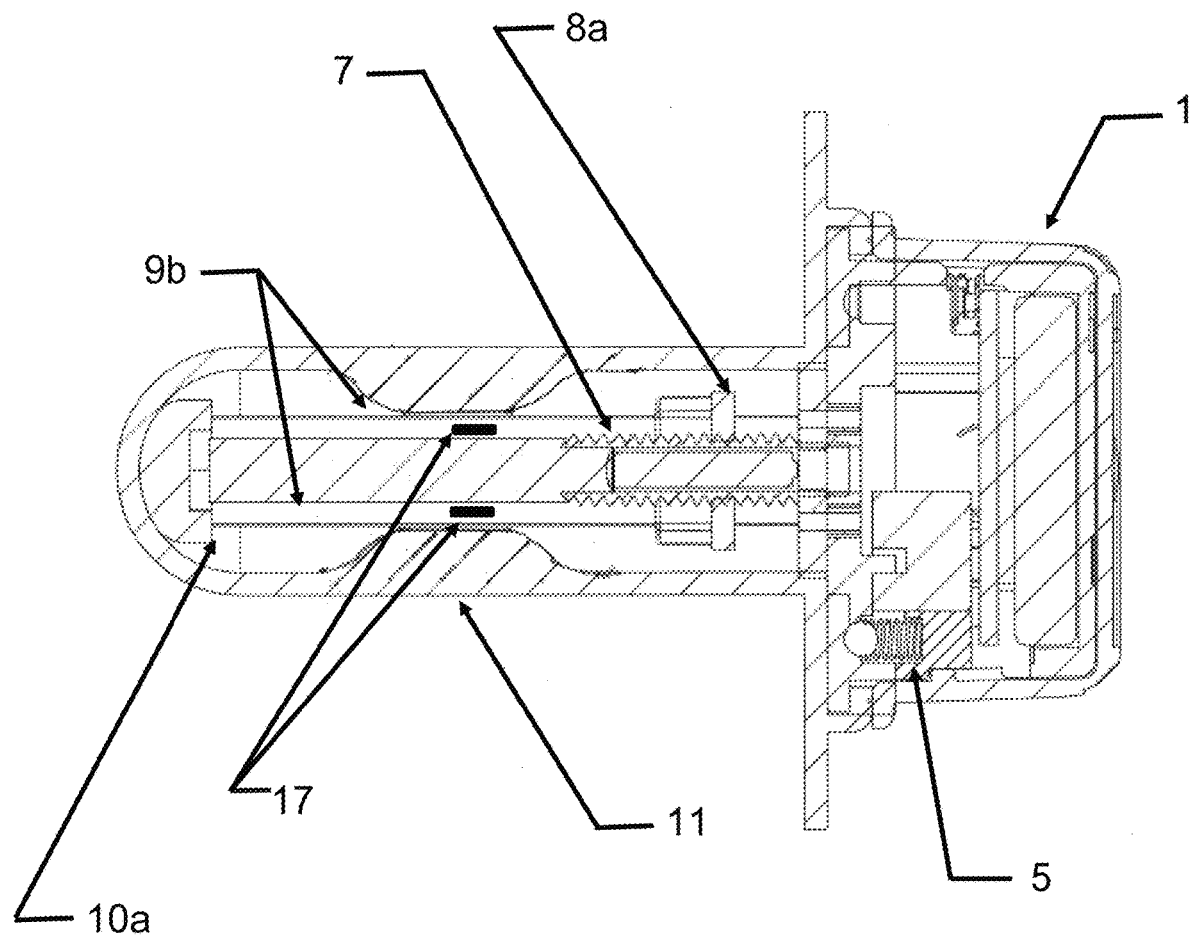
Figure 6B:
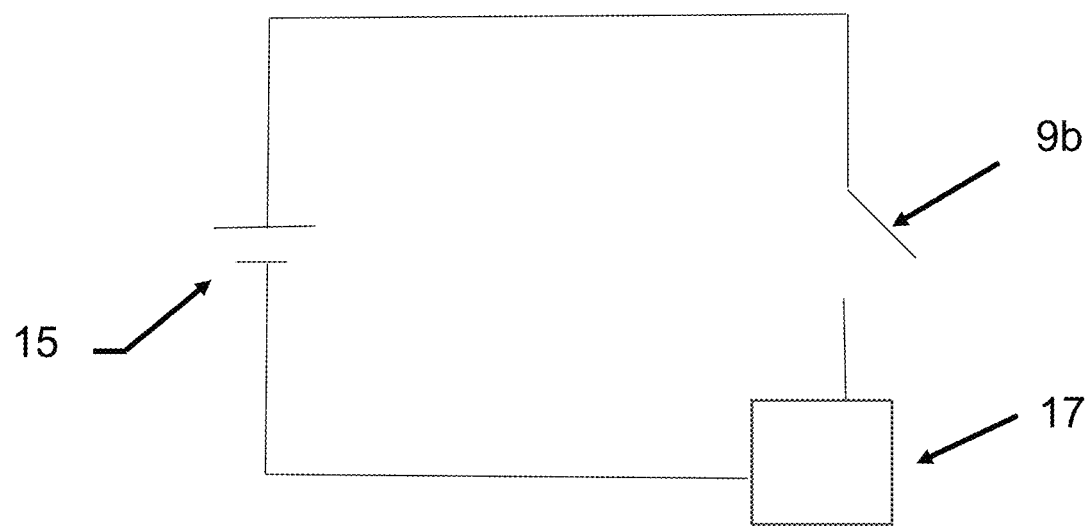
Figure 7:
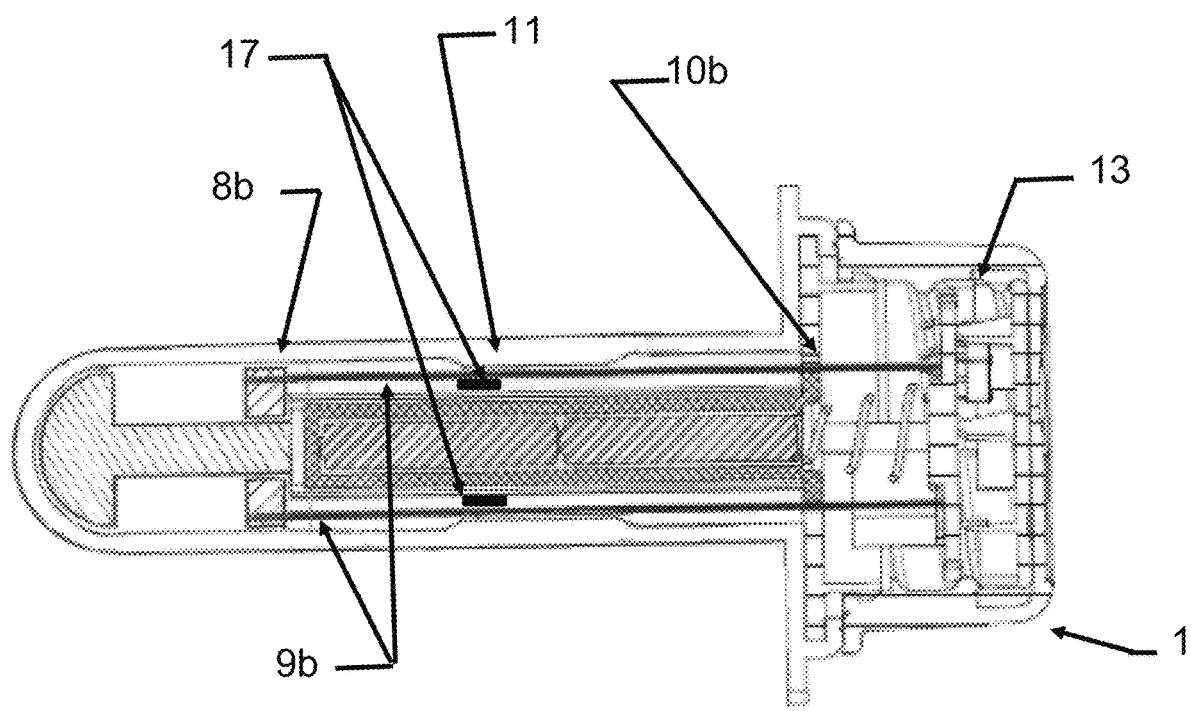
Figure 8:
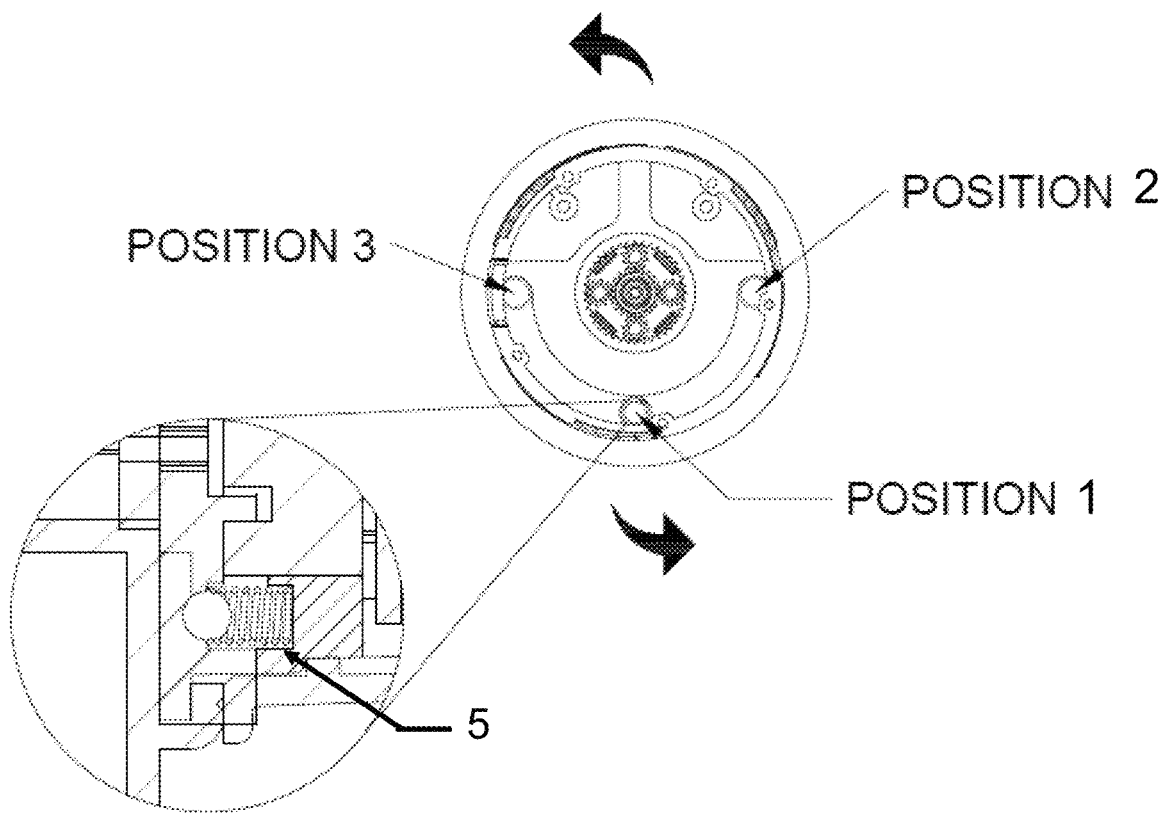
Figure 9:
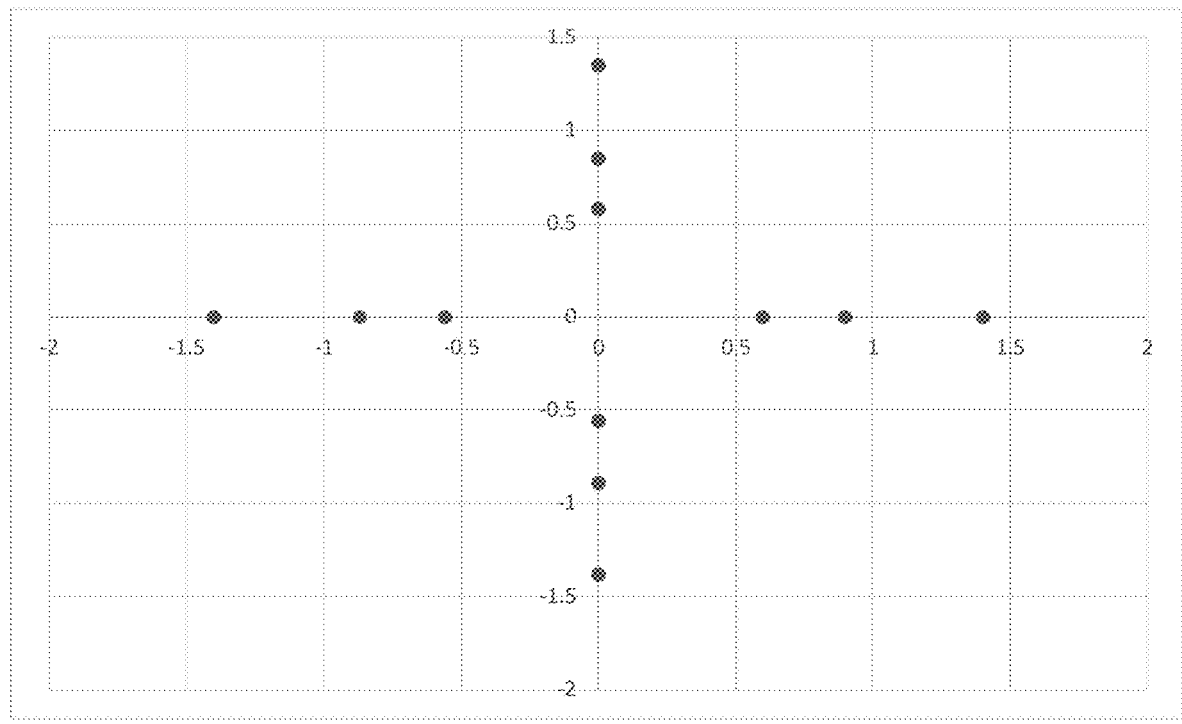
FIG. 9-13 shows force maps of a sphincter muscle wherein the y-axis and x-axis represents force exerted onto the sensors in the vertical and horizontal direction respectively or in respective directions of the sensors. A healthy sphincter muscle contraction would indicate an equal force distribution in both the y-axis and x-axis.
Figure 10:
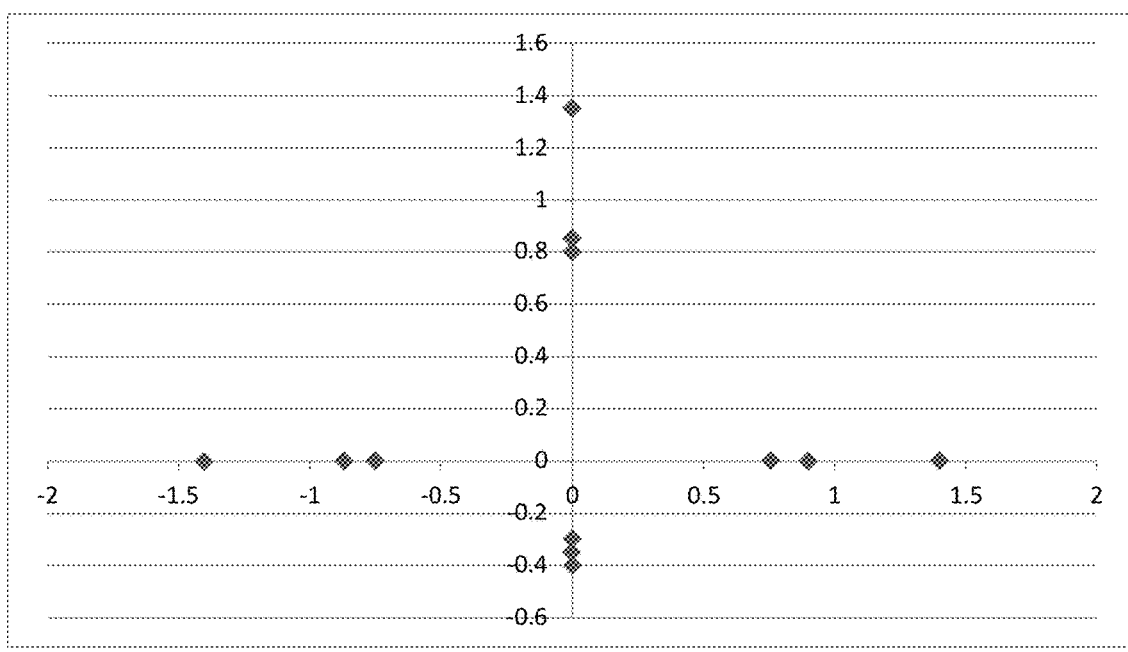

FIG. 10 shows a force map for a user with a localized tear in the sphincter muscle. The force on three of the four sides is consistent, while the force recorded from the fourth sensor is significantly lower. Muscle trauma of this type may be associated with child birth or other traumatic episode and knowledge of this condition may guide the clinician overseeing this user in appropriate care throughout recovery.

Figure 11:
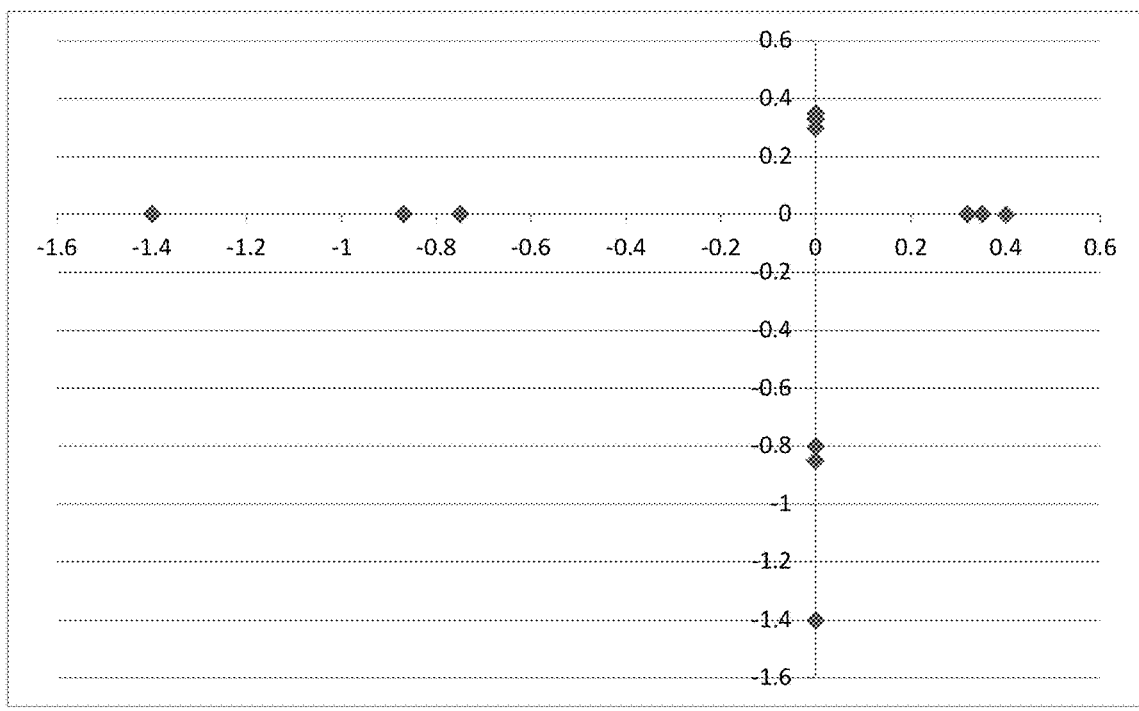

FIG. 11 shows a force map for a user with a more extensive muscular or neurological damage. In this example, it appears that half of the sphincter is not contracting or is significantly underperforming during contraction.

Figure 12:
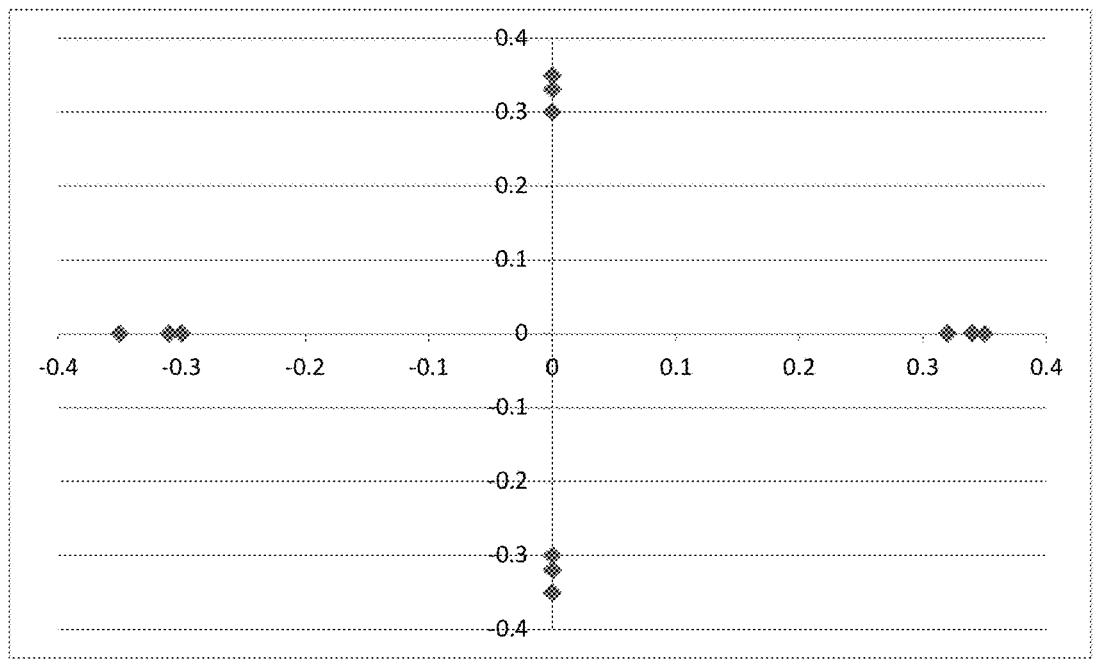

FIG. 12 shows a force map for a user after implementing exercise routine with the adjustable perineometer device. This data shows similar contractile force for each contraction, with a small fall off as would be expected as muscle fatigues.

Figure 13:
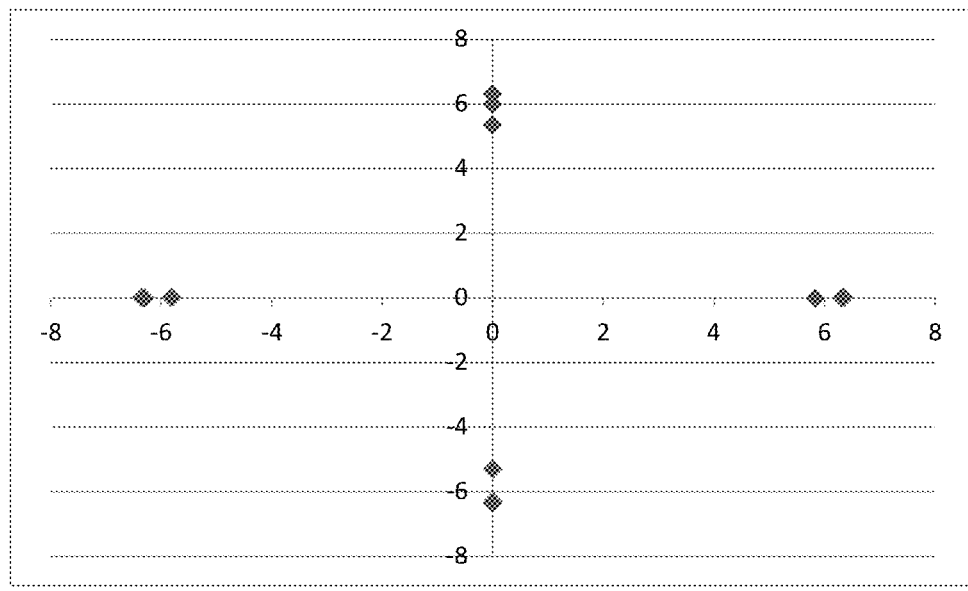

FIG. 13 shows a force map for a user with involuntary contractions (vaginismus). This plot shows a consistently high force, but also the relative health (as indicated by the radially consistency) of the sphincter. As the user learns conscious control of the muscle and learns to relax the muscle, data from the device would be helpful in showing progress and control during their recovery from this condition.

Figure 14:
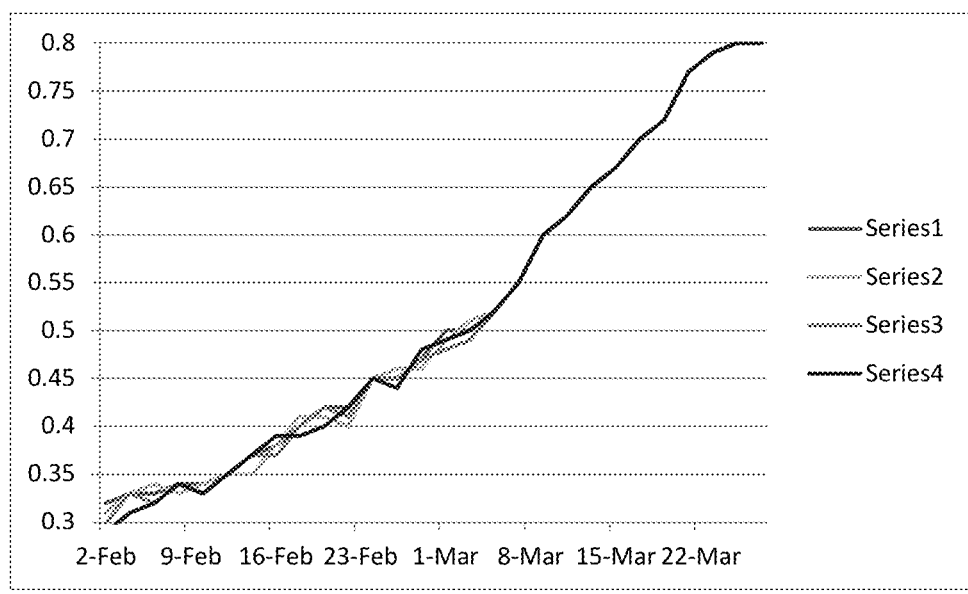

FIG. 14 shows a force graph for users following exercise routine with the adjustable perineometer device after two months. Each of the data series relates to data from different sensors of the device. Data gathered over time can help the user see progress even while symptoms may still be present to encourage continued use during recovery from their condition. In this graph, data shows consistent use and significant improvement in the strength and resiliency of the sphincter.

Figure 15:
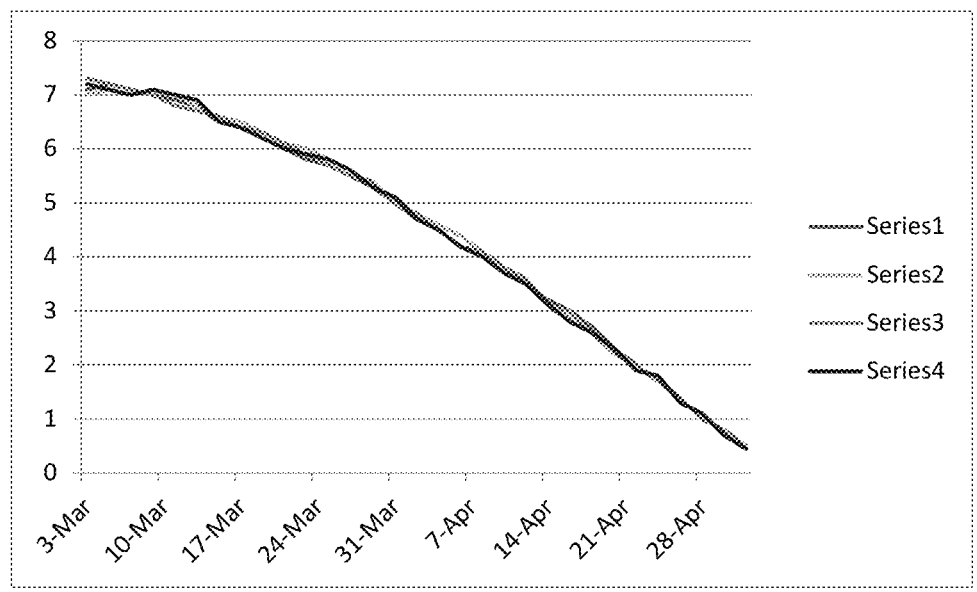

FIG. 15 shows a force graph for users suffering from vaginismus after two months. Each series indicates data from a different sensor. This graph shows data from consistent use and shows that the user is learning to relax the sphincter and recover from the condition.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises", "comprising", "including" and "having" are inclusive and therefore specify the presence of stated features, integers, steps, operations, elements and/or components, but do not preclude the presence or addition of one or more other features, integers, steps, operations, elements, components and/or groups therefrom.

The method steps, processes and operations described herein are not to be construed as necessarily requiring their performance in the particular order discussed or illustrated, unless specifically identified as an order of performance. It is also to be understood that additional or alternative steps may be employed. The use of the expression "at least" or "at least one" suggests the use of one or more elements, as the use may be in one of the embodiments to achieve one or more of the desired objects or results.

The invention claimed is:

1. A perineometer device for providing biofeedback on condition of sphincter muscle, comprising:
    a cap coupled to a tubular member; at least one first finger disposed coaxially within the tubular member;
    at least one plate disposed internally and parallel to the at least one first finger, the at least one plate spaced apart from the at least one first finger;
    at least one battery for applying an electrical potential difference to the at least one first finger and the at least one plate;
    a capacitive measuring microchip for measuring capacitance between the at least one finger and the at least one plate; and
    a processor for recording capacitance measured by the capacitive measuring microchip;
    wherein:
    the processor is communicable to a radio transmitter for transmitting capacitance value or force data to a user interface device via radio frequency; and
    the at least one first finger is retractable or extendable towards the cap when rotated in one direction, wherein stiffness of the at least one first finger is adjustable.

2. The perineometer device as claimed in claim 1, wherein when in use, force exerted on the tubular member is translatable to the at least one first finger, the at least one first finger deflectable under the force, the processor records the capacitance under deflection and calculates force exerted on the at least one first finger.

3. The device as claimed in claim 1, wherein the at least one first finger is contactable or securable to the inner surface of the tubular member.

4. The device as claimed in claim 1, wherein the device comprises a plurality of first fingers and a corresponding number of plates.

5. The device as claimed in claim 1, wherein the force data are force calculations to create force maps corresponding to muscle contraction.

6. The device as claimed in claim 1, wherein retracting or extending the at least one first finger changes force range measured by the capacitive measuring microchip.

7. The device as claimed in claim 1, wherein the at least one first finger and at least one plate form individual segments connected end to end and the individual segments are supported by a spring attachable to each end of the at least one plate via a slidable guide so that the spring is slidable up and down to apply varying amounts of physical resistance to the at least one plate from 0 N to a desired amount of force by way of an extension and retraction mechanism.

8. A perineometer device for providing biofeedback on condition of sphincter muscle, comprising:
    a cap coupled to a tubular member;
    at least one finger disposed coaxially within the tubular member;
    at least one force sensing resistor contactable to the at least one finger such that force applied to the at least one finger is measured by the at least one force sensing resistor; and
    a processor for recording resistance measured by the at least one force sensing resistor,
    wherein:
    the processor is connected to a radio transmitter for transmitting resistance value or force data to a user interface device via radio frequency; and the at least one finger is retractable or extendable towards the cap when rotated in one direction, wherein stiffness of the at least one finger is adjustable.

9. The perineometer device as claimed in claim 8, wherein when in use, force exerted on tubular member is translatable to the at least one finger, the at least one finger deflectable under the force, the processor records the resistance under force and calculates force exerted on the at least one second finger.

10. The perineometer device as claimed in claim 8, wherein the force sensing resistor is replaceable with an accelerometer or an eddy current sensor.

11. The device as claimed in claim 8, wherein the at least one finger is contactable or securable to the inner surface of the tubular member.

12. The device as claimed in claim 8, wherein the device comprises a plurality of fingers and a corresponding number of force sensing resistors.

13. The device as claimed in claim 8, wherein the force data are force calculations to create force maps corresponding to muscle contraction.

14. The device as claimed in claim 8, wherein retracting or extending the at least one finger changes force range measured by the force sensing resistor.

15. The device as claimed in claim 8, wherein a spring is attachable in between the at least one finger and force sensing resistor via a slidable guide so that the spring is slidable up and down to apply varying amounts of physical resistance to the at least one force sensing resistor from 0 N to a desired amount of force by way of an extension and retraction mechanism.

16. The device as claimed in claim 8, wherein the cap comprises a port for connecting to a user device through a wired connection such that if user interface featured on the cap and/or radio transmitter is faulty, data is receivable and transmittable to user device connected.

\* \* \* \* \*